(12) United States Patent
Gu et al.

(10) Patent No.: US 9,675,540 B2
(45) Date of Patent: *Jun. 13, 2017

(54) ORAL COMPOSITIONS AND METHOD FOR PRODUCING THEREOF

(75) Inventors: Ben Gu, East Brunswick, NJ (US); Mahmoud Hassan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/993,719

(22) PCT Filed: Dec. 13, 2010

(86) PCT No.: PCT/US2010/060114
§ 371 (c)(1),
(2), (4) Date: Jun. 13, 2013

(87) PCT Pub. No.: WO2012/082103
PCT Pub. Date: Jun. 21, 2012

(65) Prior Publication Data
US 2013/0266523 A1 Oct. 10, 2013

(51) Int. Cl.
*A61K 8/73* (2006.01)
*A61Q 11/00* (2006.01)
*A61K 8/92* (2006.01)

(52) U.S. Cl.
CPC .............. *A61K 8/731* (2013.01); *A61K 8/922* (2013.01); *A61Q 11/00* (2013.01)

(58) Field of Classification Search
CPC combination set(s) only.
See application file for complete search history.

(56) References Cited

U.S. PATENT DOCUMENTS

| | | | |
|---|---|---|---|
| 3,507,955 A * | 4/1970 | Osipow | 424/54 |
| 4,590,065 A | 5/1986 | Piechota, Jr. et al. | |
| 4,713,243 A | 12/1987 | Schiraldi et al. | |
| 4,894,220 A | 1/1990 | Nabi et al. | |
| 5,330,748 A * | 7/1994 | Winston et al. | 424/49 |
| 5,976,507 A | 11/1999 | Wong et al. | |
| 6,258,342 B1 | 7/2001 | Harcum et al. | |
| 6,379,654 B1 | 4/2002 | Gebreselassie et al. | |
| 6,419,903 B1 | 7/2002 | Xu et al. | |
| 6,419,906 B1 | 7/2002 | Xu et al. | |
| 6,514,483 B2 | 2/2003 | Xu et al. | |
| 6,669,929 B1 | 12/2003 | Boyd et al. | |
| 7,671,100 B2 | 3/2010 | Gaserod et al. | |
| 2004/0042976 A1 | 3/2004 | Silber et al. | |
| 2004/0062724 A1 | 4/2004 | Moro et al. | |
| 2004/0126332 A1 | 7/2004 | Boyd et al. | |
| 2004/0136924 A1 | 7/2004 | Boyd et al. | |
| 2005/0019273 A1 | 1/2005 | Boyd et al. | |
| 2005/0106112 A1 * | 5/2005 | Boyd et al. | 424/49 |
| 2006/0062809 A1 | 3/2006 | Six et al. | |
| 2007/0140985 A1 | 6/2007 | Boyd et al. | |
| 2007/0253919 A1 * | 11/2007 | Boyd | 424/54 |
| 2008/0014224 A1 | 1/2008 | Boyd et al. | |
| 2012/0070478 A1 | 3/2012 | Boyd et al. | |

FOREIGN PATENT DOCUMENTS

CN 101406436 A 4/2009
WO WO 94/26244 11/1994

OTHER PUBLICATIONS

Przybylski, R., Mag, T., Eskin, N. and McDonald, B. 2005. Canola Oil. Bailey's Industrial Oil and Fat Products. pp. 61-121.*
International Search Report and Written Opinion in International Application No. PCT/US10/060114, mailed Nov. 24, 2011.
Written Opinion in International Application No. PCT/US10/060114.

* cited by examiner

*Primary Examiner* — David J Blanchard
*Assistant Examiner* — Nicole Babson

(57) ABSTRACT

Methods of preparing a dentifrice comprising polymer matrix film with menthol therein are disclosed. The methods comprise combining a polymer matrix film that comprises hydrophobic additives and is free of a low solubility flavorant such as menthol with a dentifrice base comprising a low solubility flavorant such as menthol and maintaining the combined polymer matrix film with the dentifrice base comprising low solubility flavorant for an amount of time sufficient for an amount of a low solubility flavorant to transfer from the dentifrice base comprising low solubility flavorant to the polymer matrix film and establish an equilibrium of menthol concentration between the polymer matrix film and the dentifrice base. Products comprising low solubility flavorant-free polymer matrix film in a dentifrice base comprising low solubility flavorant are also disclosed.

13 Claims, No Drawings

US 9,675,540 B2

ORAL COMPOSITIONS AND METHOD FOR PRODUCING THEREOF

FIELD OF THE INVENTION

This invention relates to methods of making dentifrice products comprising hydratable, polymer matrix film that include low solubility flavorants.

BACKGROUND OF THE INVENTION

The hydratable, polymer matrix films, which comprise hydrophobic/lipophilic additives and are produced free of low solubility flavorants are combined with dentifrice base that comprises low solubility flavorant which migrates from the dentifrice base into the hydratable, polymer matrix films to form a dentifrice that comprises hydratable, polymer matrix films which include low solubility flavorants.

Liquid, gel and semi-solid oral care products which comprise hydratable, polymer matrix films containing low solubility flavorants such as menthol are known. Hydratable, polymer matrix film containing low solubility flavorants such as menthol are prepared and added into toothpaste to generate an aesthetic effect as well as to provide the benefit of a flavor and/or cooling sensation or signal. The hydratable, polymer matrix film, typically in the form of flakes or small sized pieces cut from larger manufactured films, is maintained in the product when stored. Upon use, the films typically degrade by chemical or physical disruption, thereby releasing the active or functional material into the surrounding environment. In this manner, the films provide an opportunity for localized release of a high concentration of active materials, such as for example zinc oxide, near a target surface. In addition, low solubility flavorant in the film is also released. The low solubility flavorants such as menthol in the films provide an extended flavor experience to the user compared to that which occurs when compositions in which the flavor is only in the toothpaste base are used. By including flavorants in the films, flavor may be released from films during and immediately after use, providing a flavor experience that continues after performance of the oral care process such as brushing or rinsing is completed. This extended experience can be pleasing.

Conventional methods of manufacturing hydratable, polymer matrix films that contain low solubility flavorants such as menthol comprise the step of incorporating menthol into the slurry that is then used to form the film. The low solubility flavorant is thereby dispersed throughout the slurry which is used to make the film. After the film is formed, it is typically often cut into flakes or pieces, and introduced into the toothpaste base. The step of adding relatively insoluble flavorant into the slurry used to manufacture the hydratable, polymer matrix films typically requires the use of solvents such as ethanol. When making the films, the ethanol is typically removed using heat which causes the ethanol to evaporate. The low solubility flavorants are lost as a result of evaporation of the ethanol solvent. For examples, about 50% of menthol in a slurry formula is lost with the solvent when the ethanol evaporates. Moreover, the evaporated ethanol creates a safety concern in the manufacturing facility. Accordingly, introduction of low solubility flavorants into the film during its manufacture is inefficient, which leads to in additional manufacturing costs, and creates conditions which must be managed to avoid safety problems.

There is a need for improved methods of manufacturing liquid, gel and semi-solid oral care products which comprise hydrophilic films containing menthol.

BRIEF SUMMARY OF THE INVENTION

Methods of manufacturing dentifrices which comprise hydratable polymer matrix films that contain relatively water insoluble flavorants such as menthol are provided. Flavorant free hydratable polymer matrix films which comprise hydrophobic additives are produced and added to dentifrice base that contains flavorant. The flavorant from the dentifrice base is taken up in situ by the flavorant free films. This in situ method of introducing flavorant into hydratable polymer matrix films that comprise hydrophobic additives simplifies the manufacturing process, improves safety and reduces cost.

Some aspects provide dentifrice compositions comprising low solubility flavorant-free polymer matrix film in a dentifrice base comprising low solubility flavorant

DETAILED DESCRIPTION OF THE INVENTION

Definitions

As used herein, the term "cellulose polymer" is meant to refer to cellulose and cellulose derivatives such as cellulose ester derivative and cellulose ether derivatives.

As used herein, the term "dentifrice" includes toothpastes and gels.

As used herein, such a "pharmaceutically acceptable" or "cosmetically acceptable" component is one that is suitable for use with humans and/or animals to provide the desired therapeutic, prophylactic, sensory, decorative, or cosmetic benefit without undue adverse side effects (such as toxicity, irritation, and allergic response) commensurate with a reasonable benefit/risk ratio.

As used herein, the term "polymer matrix film" is meant to refer to the product of a process wherein cellulose and derivatives thereof are used in combination with other polymers to form thin solid water hydratable film which may further comprise other components including, colloidal particles. The polymer matrix film comprises one or more hydrophobic/lipophilic additives. The polymer matrix film for example may further comprise additives such as, for example, colorants, water soluble flavorants, sweeteners, breath fresheners, whitening agents, and/or therapeutic agents such as agents that promote oral health, e.g. healthy teeth, gums and other oral tissue, and agents that prevent and treat various oral maladies. In addition, the polymer matrix film may include other film forming agents, plasticizing agents, surfactants and emulsifying agents. The polymer matrix film may be cut or otherwise divided into multiple pieces such as flakes or small strips and added to a dentifrice where they may provide aesthetic elements and/or serve as a carrier for one or more additives which may be included.

As used herein, the term "low solubility flavorant" refers to a flavor ingredient or cooling agent which is relatively insoluble in water, i.e. having the solubility generally on the order of menthol in water or less soluble. A "low solubility flavorant" must first be incorporated into a solution using a solvent such as an alcohol, particularly ethanol, in order to stably incorporate it into the slurry of hydrophilic hydratable polymer which can be used to produce hydratable polymer matrix films comprising low solubility flavorants.

As used herein, the term "low solubility flavorant-free polymer matrix film" is meant to refer to a polymer matrix film that is in the substantial absence of low solubility flavorant. Low solubility flavorant-free polymer matrix films are produced without the direct addition of low solubility flavorant, or of ingredients or solutions containing low solubility flavorant into the slurry used to make the low solubility flavorant-free polymer matrix film.

As used herein, the term "substantial absence" is meant to refer to a film that has a low solubility flavorant content on film formation of less than 0.5%.

As used herein, the term "transferring" refers to migration, moving or transporting flavorant from the dentifrice base into the film. Passive transfer typically does not require an external agent (e.g., mechanical force, chemical and/or thermal energy) to achieve movement of the low solubility flavorant. Passive transfer typically encompasses mass transport phenomena including diffusion, where the flavorant molecules are physically transported across a concentration gradient to approach thermodynamic equilibrium. Further, passive transfer may include electrochemical interaction, absorption, adsorption, and/or wicking movement of the flavorant into the film, where application of an external agent is not required to achieve sufficient movement of the flavorant into the film. Active transport is generally not required. However, in some embodiments, ingredients may be provided to drive equilibrium to promote transfer of flavorant from the dentifrice base to the polymer matrix film.

Throughout the present disclosure, ranges are used as shorthand for describing each and every value that is within the range. Any value within the range can be selected as the terminus of the range. Furthermore, all references cited throughout the disclosure are expressly incorporated by reference in their entireties. As used herein, all references to concentration of ingredients are on a weight basis, unless otherwise indicated.

Unless otherwise specified, all percentages and amounts expressed herein and elsewhere in the specification should be understood to refer to percentages by weight. The amounts given are based on the active weight of the material.

Overview

Aspects of the present invention relate to methods of making a gel and semi-solid oral care products such as toothpaste which comprise polymer matrix films that contain low solubility flavorant such as menthol. The polymer matrix films comprise one or more hydrophobic/lipophilic additives. Some of the methods comprise producing a low solubility flavorant-free hydratable polymer matrix and eliminating the use of alcohol that is required when incorporating low solubility flavorant into the polymer slurry used to make polymer matrix films. The low solubility flavorant-free hydratable polymer matrix film is combined with a dentifrice base that comprises a low solubility flavorant and the low solubility flavorant transfers from the dentifrice base into the polymer matrix film. Thus, after being combined with the dentifrice base that comprises low solubility flavorant, flavorant becomes incorporated into what was formerly low solubility flavorant-free polymer matrix film and the resulting combination includes polymer matrix films that comprise low solubility flavorant dispersed in dentifrice base. The low solubility flavorant is transferred from dentifrice base into the polymer matrix film such that the polymer matrix film contains flavorant at a concentration nearly equal to, equal to or greater than the concentration of flavorant in the base. The transferred flavorant is stable during storage of the composition. The hydrophobic/lipophilic additive serves to promote the transfer of low solubility flavorant into the polymer matrix film and to maintain the concentration of the low solubility flavorant in the polymer matrix film was transfer has occurred. The transferred flavorant is stable during storage of the composition.

In various embodiments, the invention provides methods which eliminate a step performed in the conventional process of making dentifrice products that comprise polymer matrix films which include low solubility flavorant such as menthol. The step that may be eliminated is a step involving making a flavorant solution having low solubility flavorant in a solvent such as ethanol or another alcohol or solvent system. In the conventional process, the flavorant solution is included in the slurry that is processed into the polymer matrix film. The alcohol used to incorporate the low solubility flavorant into the slurry is removed by evaporation. By removing the alcohol in this way, low solubility flavorant is lost from the slurry with the alcohol in the evaporation process, resulting in the actual amount of low solubility flavorant in the polymer matrix films to be less than the amount of low solubility flavorant added to the slurry. This loss increases costs and the need for larger amounts of low solubility flavorant. Moreover, steps must be taken to prevent any hazards that may arise in the manufacturing process due to evaporated alcohol in the manufacturing facility.

Thus, in the conventional method, the polymer matrix films contain low solubility flavorant prior to their addition to the dentifrice base. The preparation and use of an alcohol-based solution is eliminated by producing low solubility flavorant-free polymer matrix films and combining them into dentifrice base that comprises a solubility flavorant. The low solubility flavorant-free polymer matrix films comprise a hydrophobic/lipophilic component. When included in a dentifrice base that comprises low solubility flavorant, the flavorant migrates from the base into the polymer matrix films. The resulting product is a dentifrice having hydratable, polymer matrix films which comprise low solubility flavorant. The modification of the conventional process reduces costs of materials and eliminates potential safety issues that exist when using ethanol solutions.

Polymer Matrix Films

Polymer matrix films provided herein comprise one or more species of water soluble polymers such as cellulose polymers, other polysaccharides and other polymers which are generally hydrophilic. Polymer matrix films also comprise one or more hydrophobic/lipophilic additives, typically hydrophobic/lipophilic polymers, and may also comprise numerous other ingredients.

Typically, polymer matrix films comprise polymers present in an amount between 30% and 90% of the polymer matrix film's dry weight. The polymers may be present in an amount of between 40% and 80% of the polymer matrix film's dry weight. Some embodiments comprise polymers in an amount between 40% and 70% of the polymer matrix film's dry weight. Some embodiments comprise polymers an amount between 40% and 60% of the polymer matrix film's dry weight. Some embodiments comprise polymers an amount between 40% and 50% of the polymer matrix film's dry weight. Some embodiments comprise polymers in an amount between 50% and 80% of the polymer matrix film's dry weight. Some embodiments comprise polymers an amount between 60% and 80% of the polymer matrix film's dry weight. Some embodiments comprise polymers an amount between 65% and 75% of the polymer matrix film's dry weight.

Films useful for the present invention may be rigid or flexible, comprising any of a variety of materials, including film forming materials. In some embodiments, the film comprises at least one film-forming material, preferably comprising a polymer. Useful polymers include hydrophilic polymers, i.e. polymers soluble in a solvent, such as water. A water-soluble polymer that dissolves during exposure to water and application of physical force during use (such as during tooth brushing or scrubbing with a brush or pad) is desirable. Where the polymer does not fully break down during use, it may be a water-repellant polymer or an aqueous-stable hydrophilic polymer such as certain types of cellulose, e.g., paper. Examples of useful polymers are described in U.S. Pat. No. 4,713,243 to Schiraldi et al., U.S. Pat. Nos. 6,419,903, 6,419,906, 6,514,483 all to Xu, and U.S. Pat. No. 6,669,929 to Boyd et al.; United States Patent Publication Nos. 2004/0126332, 2004/0136924, and 2004/0042976 all to Boyd et al., and 2004/0062724 to Moro et al.

The polymer matrix film is hydratable, comprises a hydrophobic/lipophilic additive and it may for example, and is free of low solubility flavorants. The relative amounts of water-soluble or hydrophilic polymers and or hydrophobic/lipophilic additive may be selected to control transfer and concentration of low solubility flavorants from dentifrice base to polymer matrix film. Additionally, the formulation of the polymer matrix films may be selected to affect release of active ingredient such as the amount released proportional to how vigorously or how long the composition is used, e.g., by brushing, scrubbing, or other mechanical action during use of the aqueous composition. The formulation of the polymer matrix films may be selected to produce an overall delayed and/or extended release of flavorant, thereby providing a flavor experience following product use.

Polymers

One or more species of water soluble polymers may be used to manufacture the polymer matrix films provided herein. Water soluble cellulose derivatives are typically the primary type of polymer. Other types of polymers, however, may be included and in some cases in place of or at higher levels than cellulose derivatives.

Cellulose polymers are well known as is their use in water hydratable polymer matrix films. Cellulose polymers may be water soluble or water insoluble. Examples of cellulose derivatives include, but are not limited to: hydroxyalkyl methyl celluloses such as hydroxypropyl methyl cellulose, hydroxybutyl methyl cellulose, hydroxyethyl methyl cellulose, hydroxymethyl methyl cellulose and hydroxyethylpropyl methyl cellulose; carboxyalkyl methylcelluloses such as carboxypropyl methyl cellulose, carboxybutyl methyl cellulose, carboxyethyl methyl cellulose, carboxymethyl methyl cellulose and carboxyethylpropyl methyl cellulose; hydroxyalkyl celluloses such as hydroxypropyl cellulose, hydroxybutyl cellulose, hydroxyethyl cellulose, hydroxymethyl cellulose and hydroxyethylpropyl cellulose; alkyl celluloses such as propyl cellulose, butyl cellulose, ethyl cellulose (Ethocel™), methyl cellulose (Methocel™); and carboxyalkyl celluloses such as carboxypropyl cellulose, carboxybutyl cellulose, carboxyethyl cellulose, carboxymethyl cellulose and carboxyethylpropyl cellulose. Cellulose and cellulose ether derivative polymers may be of any length or combination of lengths. Moreover, the ranges of percent of substitutions may vary to ranges up to about 100%. In molecules comprising two or more different substituting groups, the percentage substitution for each group is independent of the other groups. Water hydratable polymer matrix films may comprise a single polymer type of cellulose or cellulose ether derivative, or may comprise a combination of one or more of cellulose and cellulose ether derivatives.

One or more species of water soluble polymers may be used to manufacture the polymer matrix films provided herein. Examples of water soluble cellulose polymers include hydroxypropyl methyl cellulose (HPMC), hydroxypropyl cellulose (HPC), hydroxyethyl cellulose (HEC), methyl cellulose (MC), carboxymethyl cellulose (CMC), and mixtures thereof. Typically, hydroxypropyl methyl cellulose (HPMC) and/or methyl cellulose (MC) is used. A family of HPMC and MC products is available commercially from the Dow Chemical Company under the trade designation Methocel™. HPMC products of the Methocel™ family are referred to with the suffix E, F, J or K.; MC products of the Methocel™ family are referred to with the suffix A. The number following the letter suffix refers to viscosity in millipascal-seconds (mPa-s) measured at a 2% concentration in water at 20° C. A "C" after the number refer to "hundred"; an "M" refers to "thousand". Suffix thereafter are additional identifiers, e.g. "P'" refers to "Premium", "LV'" refers to "Low Viscosity", etc. In some embodiments, one or more Methocel™ products, or generic versions thereof, may be used.

In some embodiments, HPMC is used. In some embodiments, the film forming agent used to prepare the hydratable polymer matrix films is a cellulose ether polymer such as low viscosity HPMC. When HPMC is used as the film forming agent, it is preferred that the HPMC have a viscosity in the range of about 1 to about 40 millipascal seconds (mPas) as determined as a 2% by weight aqueous solution of the HPMC at 20° C. using a Ubbelohde tube viscometer. In some embodiments, the HPMC has a viscosity of about 3 to about 20 mPas at 20° C. In some embodiments, the HPMC is Methocel™ E5 LV. Methocel™ E5 LV is a USP grade, low viscosity HPMC having 29.1% methoxyl groups and 9% hydroxyproxyl group substitution. It is a white or off-white free-flowing dry powder. As a 2 wt. % solution in water as measured with an Ubbelohde tube viscometer, the HPMC solution has a viscosity of 5.1 mPas at 20° C. Other examples of METHOCEL™ HPMC products include METHOCEL™ E5, METHOCEL™ E50, METHOCEL™ E15, and METHOCEL™ K100.

Water soluble cellulose derivatives are typically the primary type of polymer. Other types of polymers, however, may be included and in some cases in place of or at higher levels than cellulose derivatives. Other useful polymers may include polyvinylpyrrolidone (PVP), which can have a weight average molecular weight of about 100,000 or more and up to about 1.5 million, vinyl acetate, polyvinylpyrrolidone-vinyl acetate copolymers such as KOLLIDON™ VA64 (available from BASF, 60:40 by weight vinyl pyrrolidone) and PLASDONE™ S630 PVP (available from International Specialty Products, Wayne, N.J., United States of America, 60:40 by weight vinyl pyrrolidone:vinyl acetate), ethylene oxide graft copolymers of PVA such as KOLLICOAT™ IR (available from BASF, 75% by weight PVA, 25% by weight polyethylene glycol graft, polyvinyl alcohol (PVA), acrylates and polyacrylic acid, including polyacrylate polymer, cross-linked polyacrylate polymer, cross-linked polyacrylic acid (e.g., CARBOPOL™), vinylcaprolactam/sodium acrylate polymers, methacrylates, maleic poly vinylalkyl ether-maleic acid copolymer (e.g., GANTREZ™), vinyl acetate and crotonic acid copolymers, polyacrylamide, poly(2-acrylamido-2-methylpropane sulfonate), terpolymers of acrylomethyl propyl sulphonic acid/methylacrylate/styrene monomers, phosphonate styrene polymers, polyethylene phosphonate, polybutene phosphonate, polystyrene, polyvinylphosphonates, polyalkylenes, polyalkylene oxides, including polyethylene oxide, i.e. polyethylene glycol, and carboxy vinyl polymer. As appreciated by a skilled artisan, the film may comprise derivatives, copolymers, and further mixtures of such polymers as well.

Useful water-insoluble polymers include polymers soluble in at least one organic solvent; for example, acrylic copolymers (where carboxylic acid functionality has not been neutralized), cross-linked poly(vinyl pyrrolidone), for example KOLLIDON™ CL or CL-M available from BASF, poly(vinyl acetate) (PVAc), certain cellulose derivatives such as cellulose acetate, cellulose nitrate, alkyl cellulose such as ethyl cellulose, butyl cellulose, and isopropyl cellulose, cellulose acetate phthalate, shellac, ethylene-vinyl acetate copolymers, vinyl acetate homopolymer, silicone polymer (e.g., dimethylsilicone), polymethyl methacrylate (PMMA), polymers insoluble in organic solvents, such as cellulose, polyethylene, polypropylene, polyesters, polyurethane and nylon, natural or synthetic rubber, and mixtures thereof. An example of a suitable, film-forming acrylic copolymer is LUVIMER™ 30E, a 30% by weight solution in ethanol of a tert-butyl acrylate/ethyl acrylate/methyacrylic acid copolymer commercially available from BASF (Florham Park, N.J., United States of America). The water-insoluble polymers may be prepared as dispersions (e.g., by emulsion polymerization) and may be stabilized with suitable emulsifiers. One useful PVAc emulsion, for example, is KOLLICOAT™ SR 30D, a 30 weight % dispersion of PVAc in water stabilized with 2.7 weight percent PVP and 0.3% sodium lauryl sulfate. An example of an acrylic copolymer dispersion is KOLLICOAT™ EMM 30D, a 30% by weight aqueous dispersion of an ethyl acrylate: methyl methacrylate copolymer (weight ratio of ethyl acrylate to methyl methacrylate approximately 2 to 1) with a reported average molecular weight of about 800,000, available from BASF.

Other useful polymers or water-soluble fillers include, without limitation, natural gums such as sodium alginate, carrageenan, xanthan gum, gum acacia, Arabic gum, guar gum, pullulan, agar, chitin, chitosan, pectin, karaya gum, zein, hordein, oliadin, locust bean gum, tragacantha and other polysaccharides; starches such as maltodextrin, amylose, high amylose starch, corn starch, potato starch, rice starch, tapioca starch, pea starch, sweet potato starch, barley starch, wheat starch, waxy corn starch, modified starch (e.g., hydroxypropylated high amylose starch), dextrin, levan, elsinan and gluten; and proteins such as collagen, whey protein isolate, casein, milk protein, soy protein, keratin, and gelatin. The film may further include dispersible or swellable fillers such as modified starch, alginate esters, and divalent or multivalent ion salts of alginates.

Optionally, cold water swellable, physically modified and pregelatenized starches may be used as additives that can function as a texture modifier to increase the stiffness of the polymer film matrix. In the preparation of such starch products, the granular starch is cooked in the presence of water and possibly an organic solvent at a temperature not higher than 10° C. higher than the gelatinization temperature. The obtained starch is then dried. Pregelatinized corn starch is available commercially. A useful starch is available under the trade designation Cerestar Polar Tex-Instant 12640 from the Cerestar Company. This Cerestar starch is a pregelatenized, stabilized and crosslinked waxy maize starch. It is readily dispersible and swellable in cold water. In its dry form, the starch is a white free flowing powder with an average flake size no greater than 180 micrometers and 85% of the flakes are smaller than 75 micrometers. It has a bulk density of 44 lbs/ft$^3$. The Cerestar starch has excellent cold storage and freeze-thaw stability. It has a rapid hydration rate and can reach extremely high viscosity without cooking. It has a smooth and creamy texture similar to cook-up starches. It also has excellent paste clarity and a bland flavor. The pregelatinized starch may present in the film matrix in an amount ranging from about 5 to about 20% by weight, and in some embodiments in which it is included, about 10 to about 15% by weight. In some embodiments in which starch is included, the cellulose/cellulose derivative to starch ratio (by weight) may vary from about 1:3 to about 4:1 and preferably about 1:1.5 to about 2.5:1.

In an aqueous composition, the relative amounts of water-soluble polymer and water-insoluble and/or partially water-soluble polymer in the film are preferably such that the film is storage-stable in an aqueous composition but disintegrates during use of the composition. In various embodiments, the film includes an amount of water-soluble polymer that is about 50% to 90% weight of the dry film. In some embodiments, the film includes an amount of water-soluble polymer that is about 55% to 85% weight of the dry film. In some embodiments, the film includes an amount of water-soluble polymer that is about 60% to 80% weight of the dry film. In some embodiments, the film includes an amount of water-soluble polymer that is about 65% to 75% weight of the dry film. In addition to, or instead of, the water-soluble polymer (s), in some embodiments the film may include partially water-insoluble or water-swellable polymers in amounts of about 0.1% to about 50% by weight of the film, preferably about 10% to about 20% weight. In various embodiments, a method of stabilizing hydrophilic films in an aqueous carrier environment uses water-soluble and water-insoluble materials in the film that are balanced for stability while stored in the product carrier, but disintegrate upon use to release the active ingredient contained therein. In some embodiments, non-polymer materials such as colloidal metals for example may be included in the films. The polymers may be present in an amount of between 40% and 80% of the polymer matrix film's dry weight. Some embodiments comprise polymers in an amount between 40% and 70% of the polymer matrix film's dry weight. Some embodiments comprise polymers an amount between 40% and 60% of the polymer matrix film's dry weight. Some embodiments comprise polymers an amount between 40% and 50% of the polymer matrix film's dry weight.

Hydrophobic/Lipophilic Additives

Hydrophobic/lipophilic additives include compounds which can be incorporated into the polymer matrix films, particularly during manufacture and which, when in incorporated as part of a polymer matrix film, can serve to attract low solubility flavorants from the dentifrice base and concentrate them to the polymer matrix film. Illustrative examples of hydrophobic/lipophilic additives suited for inclusion into the composition include, fats and oil including but not limited to, petrolatum, silicone oil, beeswax, hydrogenated soybean oil, sweet almond oil, peanut oil, avocado oil, borage oil, palmitic acid, cacao butter, carnauba wax, castor oil, coconut oil, evening primrose oil, glycerin, glyceryl stearate, jojoba oil, camphor, Kkaolin, lanolin, cod liver oil, linseed oil, corn oil, olive oil, palm oil, paraffin, squalane, rapeseed oil, rose oil, safflower oil, sesame oil, shea butter, dimethicone silicone oil, tall oil, wheat germ oil, sunflower oil, trimethylsiloxysilicate, alkyldimethylsilyl solypropylsesquioxane, ethyl cellulose polymers, dimethiconol, trimethylsiloxysilicate, polyether-modified silicone, cross-linked polymers, polypropylsilsesquioxane, dimethicone polymers, dimethicone crosspolymer, dimethicone/vinyl dimethicone cross polymers, other fats and oils, and combinations thereof.

The hydrophobic/lipophilic additives may be present in an amount of between 1% and 20% of the polymer matrix film's dry weight. Some embodiments comprise hydrophobic/lipophilic additives in an amount between 3% and 15% of the polymer matrix film's dry weight. Some embodiments comprise hydrophobic/lipophilic additives an amount between 5% and 10% of the polymer matrix film's dry weight. Some embodiments comprise hydrophobic/lipophilic additives an amount between 1% and 8% of the polymer matrix film's dry weight.

Colloids and Colloidal Particles

In some embodiments, polymer matrix films comprise colloids. The colloid may present in an amount between 10% and 60% of the polymer matrix film's dry weight. The colloid may present in an amount between 20% and 50% of the polymer matrix film's dry weight. The colloid may present in an amount between 30% and 50% of the polymer matrix film's dry weight. The colloid may present in an amount between 40% and 50% of the polymer matrix film's dry weight.

Colloids and colloidal particles can be used to stabilize polymer matrices and fine tune its rigidity in order to provide films that are flexible enough to process, yet physically and cosmetically stable. As films are optimized, it is important to identify the parameters that will deliver optimal film performance. These parameters can be determined by quantifying the properties of the film at both the slurry stage and the dry film stage. At the slurry stage, the interactions between the polymers and the other film ingredients, including colloidal particles, form the structure of the film matrix. The viscoelastic properties of the slurry, such as the viscosity and the structural parameter (G'), enable the characterization of structural arrangement within the slurry and the processability of the same. Following processing and drying of the slurry, the bulk film is formed, setting the polymer matrix. Mechanical properties, such as the glass transition temperature, the tensile strength, and the dissolution time can be used to determine the stability of the film. By balancing the microstructural properties, such as the polymer interactions, with the macrostructural properties of the film, such as the mechanical properties, film can be made more cosmetically stable and can be better utilized as a delivery platform for various actives.

In some embodiments, colloidal particles are present in the film in the range of 40-50% dry weight.

Water-insoluble colloidal metal compounds of multivalent metals are preferred. Representative metal oxides suitable for use in the compositions described herein include silicon oxide ($SiO_2$), molybdenum oxide ($Mo_2O_3$), aluminum oxide ($Al_2O_3$), titanium oxide (TiO), zirconium oxide ($ZrO_2$) and zinc oxide (ZnO).

Particle size may be about 1 to about 1000 nm. Preferably the particles have an average particle size of about 1 μm to about 850 nm, about 50 μm to about 150 nm, about 15 nm to about 500 nm, about 30 nm to about 250 nm and/or about 5 μm to about 100 nm.

In some embodiments, the particles are non-aggregated. By non-aggregated it is meant that the particles are not massed into a cluster having a size greater than about 1 micron, preferably greater than about 950 nm or 850 nm. However, particles may be mixed with aggregated particles and other colloidal particles that have an average particle size of greater than 1 micron if desired. In some embodiments, more than 80% of particles are non-aggregated. In some embodiments, more than 90% of particles are non-aggregated.

In some embodiments, colloidal particles are provided in the dentifrice base. In some embodiments, colloidal particles are provided in the dentifrice base and the polymer matrix film. In some embodiments, colloidal particles are provided in the dentifrice base but not the polymer matrix film.

Preparation of Film Matrix

In preparing the film matrix, the polymers, hydrophobic/lipophilic additives and any of the optional ingredients, including for example, such as those set forth below as "Other Components", are dissolved or otherwise mixed into a compatible solvent to form a film forming composition. The film forming composition may contain no flavorant and no flavor solvent. The film forming composition is cast on a releasable carrier and dried to form a sheet of film matrix material. In some embodiments, the carrier material has a surface tension which allows the film solution to spread evenly across the intended carrier width without soaking to form a destructive bond between the film carrier substrates. Examples of suitable carrier materials include glass, stainless steel, Teflon and polyethylene-impregnated paper. Drying of the film may be carried out at high temperature using a drying oven, drying terminal, vacuum drier, or any other suitable drying equipment which does not adversely affect the ingredients of which the film is composed.

The slurries that are precursors to the films may be characterized using rheology. In some embodiments, the viscoelastic properties of the film slurry, as quantified using G' as an indicator of the structural character of the polymer-particle network, may be about 220-560. In some embodiments G' is about 223-550. In some embodiments, the structure of the polymer-particle matrix is not weak and the slurry is not essentially liquid-like. In some embodiments, the structure of the polymer-particle matrix is not very rigid thereby not leading to the formation of a very brittle film. In some embodiments, the viscosity profile as a function of shear rate is quantified as a measure of flowability and processability the slurries. In some embodiments, the viscosity profiles are not a semi-dilute solution. The viscosity in poise is measured at 0.3 s−1. In some embodiments, the viscosity (taken at 0.3 s−1) for the various slurries is about 175-475. In some embodiments, the viscosity (taken at 0.3 s−1) for the various slurries is about 183-450.

The films of the present invention preferably have a substantially lamellar structure. A "lamellar" structure has a size in one or two dimensions (e.g., x- or y-dimensions) that is substantially greater than the thickness of the structure in a third dimension (e.g., the z-dimension), and generally includes substantially planar, layered, or lamelliform shapes, for example. In one embodiment, the lamellar structure is substantially planar, having a size in both the x- and y-dimensions that is substantially greater than the z-dimension. In other embodiments, the lamellar structure is non-planar. In one embodiment, a film comprises a substantially continuous surface that can appear as a substantially flat surface, although in some embodiments the film may be deformed. In such embodiments, the film can have any of a number of shapes, including having a smooth, curved surface. Further, the term "film" encompasses both a single structure as well as a plurality of film fragments. In certain embodiments, the film comprises a plurality of fragments independently having a thickness of about 0.1 mils to about 10 mils, preferably about 0.5 mils to 9 mils, and more preferably about 1.2 mils to about 3 mils. In some embodiments, the film thickness range is 2 to 3 microns. A preferred length of the fragments is at least about 0.2 mm.

The dried film is then processed for inclusion in the dentifrice. The film may be cut or punched into small strips or squares. In various embodiments, the film comprises a plurality of fragments or pieces. Such fragments may be of any of a variety of shapes or forms, including semi-solid or solid discrete portions, fragments, particles, flakes, or mixtures thereof. In various embodiments, the film fragments have a recognizable shape. In some embodiments, a film fragment comprises a nonrandom shape. Such shapes include simple geometric shapes such as polygons, elliptical shapes, triangles, quadrilaterals (such as a square, a rectangle, a rhombus), pentagons, hexagons, ovals, circles, or shapes that are representative of figures, animate or inanimate objects, such as stars, hearts, gems, flowers, trees, shamrocks, letters, numbers, animals, characters, diamonds, circles and the like. The dried film may be cut or punched into shaped flakes having a particle size of 0.01 to 0.50 inches preferably 0.08 to 0.25 inches. Additional stability can be provided to the shapes formed from the dried film, by applying to the film, before shaping into flakes or small strips, a protective barrier overcoat such as a food grade shellac or ethyl cellulose.

Further, the plurality of film fragments may have different compositions, for example having a first plurality of film fragments comprising a first color, and a second plurality of film fragments comprising a second color, where the first and second colors are different from each other. Any permutation of different compositions is contemplated, for example, any number of different active ingredients in the compositions or different film compositions.

Base Dentifrice Composition

Examples of suitable carriers for oral care compositions are disclosed in U.S. Pat. No. 6,669,929 to Boyd et al., U.S. Pat. No. 6,379,654 to Gebreselassie et al., and U.S. Pat. No. 4,894,220 to Nabi et al. The dentifrice (toothpaste or gel) is typically water based. As recognized by one of skill in the art, the dentifrice optionally include other materials and mixtures thereof, including for example, such as those set forth below as "Other Components". It is understood that while general attributes of each of the above categories of materials may differ; there may be some common attributes, and any given material may serve multiple purposes within two or more of such categories of materials.

In the preparation of the base dentifrice in accordance with the present invention there is utilized an orally acceptable vehicle, including a water-phase with humectants. Humectants useful herein include polyhydric alcohols such as glycerin, sorbitol, xylitol or low molecular weight PEGs, alkylene glycol such as polyethylene glycol or propylene glycol. In various embodiments, humectants are operable to prevent hardening of paste or gel compositions upon exposure to air. In various embodiments humectants also function as sweeteners. One or more humectants are optionally present in a total amount of about 1% to about 50%, for example about 2% to about 25% or about 5% to about 15%. Humectants are present typically in amount of about 5 to about 10% by weight in water, typically, about 30 to about 80% by weight of the dentifrice, more typically about 50 to about 70% by weight.

The base dentifrice may also contain an inorganic or a natural or synthetic thickener or gelling agent. Optionally, one or more thickening agents are optionally present in a total amount of about 0.01% to about 15%, in some embodiments about 0.1% to about 10%, in some embodiments about 0.10 to about 5% by weight, in some embodiments about 0.2% to about 5% by weight and in some embodiments about 0.2 to about 1% by weight. These proportions of thickeners in the dentifrice compositions of the present invention in which the film flakes of the present invention are suspended are sufficient to form an extrudable, shape-retaining product which can be squeezed from a tube onto a toothbrush and will not fall between the bristles of the brush but rather, will substantially maintain its shape thereon. Suitable thickeners or gelling agents useful in the practice of the present invention include inorganic thickening silicas such as amorphous silicas available from Huber Corporation under the trade designation Zeodent 165, Irish moss, iota-carrageenan, polyvinylpyrrolidone, carboxyvinyl polymers, cellulosic polymers such as hydroxyethylcellulose, carboxymethylcellulose (carmellose) and salts thereof (e.g., carmellose sodium), natural gums such as karaya, xanthan, gum arabic and tragacanth, colloidal magnesium aluminum silicate, colloidal silica and mixtures thereof.

In various embodiments, an dentifrice composition is provided within a single component or phase. In other embodiments, the composition includes both a first and a second component that are separately maintained. Maintaining the components separately requires only that the components are maintained in such a way as to substantially prevent the interaction of one component of the composition with another component of the composition. Typically, a dual component oral care composition is employed where there are one or more incompatible ingredients included in the composition. For example, if the dentifrice comprises two incompatible active ingredients, it is advantageous to maintain them separately. While the films comprising active ingredients generally provide a degree of separation, there may be some migration of active from the film into the carrier, and vice versa, and as such, in some cases it may be desirable to provide an entirely separate phase. The separation of components can be accomplished through any means known or to be discovered in the art and includes chemical, physical, and mechanical means of separation of any combination of these. For example, the first and second incompatible components may be combined but certain components are separately maintained by wrapping or encapsulating one or both in a protective film, coating, capsule, micelle, etc.

The low solubility flavorant is present in the dentifrice base in concentrations of 0.025-10% by weight. Typically, low solubility flavorant is present in the base at a concentration of about 0.05 to about 7.5% based on the total weight. In some embodiments, low solubility flavorant is present in a concentration of about 0.1 to about 5% by weight, in some embodiments, about 0.5 to about 2.5% by weight, in some embodiments, about 0.75 to about 2% by weight, in some embodiments, about 1.0 to about 1.5% by weight.

Typically, to prepare the dentifrice base, water, humectants, e.g. glycerin, sorbitol polyethylene glycol are dispersed in a conventional mixer until the mixture becomes a homogeneous gel phase. Into the gel phase are added other ingredients and mixed until a homogeneous phase is obtained. Thereafter the thickener, any flavor and surfactant ingredients are added and the ingredients mixed at high speed until vacuum of about 20 to 100 mmHg.

In some embodiments, the dentifrice base comprises one or more other components selected from the group consisting of: polyethylene glycol, CMC, sodium saccharin, sodium fluoride, sorbitol (70% solution), purified water, colorant, silica zeodent, cocaamidopropyl betaine and sodium lauryl sulfate.

Low Solubility Flavorants

Menthol is contemplated to be the preferred low solubility flavorant. In addition to menthol, other low solubility flavor ingredients or cooling agents, natural or synthetic, may be incorporated into polymer matrix films using in-situ flavoring of films produced free of low solubility flavorants by adding the films produced free of low solubility flavorants into any toothpaste base which comprises the low solubility flavorants.

Flavor agents are known, such as natural and artificial flavors. These flavorants may be chosen from synthetic flavor oils and flavoring aromatics, and/or oils, oleo resins and extracts derived from plants, leaves, flowers, fruits and so forth, and combinations thereof. In addition to menthol, representative flavor oils include: spearmint oil, cinnamon oil, peppermint oil, clove oil, bay oil, thyme oil, cedar leaf oil, oil of nutmeg, oil of sage, and oil of bitter almonds. These flavor agents can be used individually or in admixture. Commonly used flavors include mints such as peppermint, artificial vanilla, cinnamon derivatives, and various fruit flavors, whether employed individually or in admixture. To be considered low solubility flavorants, the flavorants may be hydrophobic, insoluble or must be sufficiently insoluble in water so that they must be solubilized in a solvent such as ethanol or another alcohol in order to incorporate them into a slurry that can be used to produce a polymer film matrix at a practical level for use as a flavorant.

The low solubility flavorants may be present in the dentifrice base in an amount sufficient for an effective amount to be transferred from the base into the low solubility flavorant-free poly matrix films within a time period typically about 1 hour to about 7 days after the introduction of such films into the base. Hydrophobic/lipophilic additives are typically present in the dentifrice base in amounts between about 0.01% and 10% by weight. Some embodiments comprise hydrophobic/lipophilic additives present in an amount between 0.05% and 5% by weight. Some embodiments comprise hydrophobic/lipophilic additives present in an amount between 0.1% and 3% by weight. Some embodiments comprise hydrophobic/lipophilic additives present in an amount between 0.2% and 2% by weight. Some embodiments comprise hydrophobic/lipophilic additives present in an amount of 0.01%, 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1.0%, 1.1%, 1.0%, 1.2%, 1.25%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9% or 4.0% or more by weight.

Other Components

Additional components may also be included in the dentifrice base. In some embodiments, one or more additional components are provided in both the dentifrice base and the polymer matrix film. In some embodiments, one or more additional components are provided are provided in the dentifrice base but not the polymer matrix film. In some embodiments, one or more additional components are provided in the polymer matrix film but not in the dentifrice base.

Preferably, the polymer matrix film and/or the dentifrice base optionally comprises one or more of the following additional components: surface active agents, bulking agents, viscosity modifiers, surfactants, thickeners, humectants, diluents, fillers (in addition to those described above), pH modifying agents, plasticizers, fillers, waxes, texture modifiers, oils, flavoring and/or sweetening agents, colorants, dyes, whitening agents, breath freshening agents, abrasives, polishing agents, preservatives, solvents, and mixtures thereof. In embodiments prophylactic and therapeutic agents such as: cetylpyridinium chloride, chlorhexidene, fluoride ion sources, stannous ion sources, tartar control (anticalculus) agents, antimicrobial (e.g., antibacterial) agents, antioxidants, saliva stimulating agents, antiplaque (e.g., plaque disrupting) agents, anti-inflammatory agents, H2 antagonists, desensitizing agents, nutrients, proteins and combinations and mixtures thereof. It is understood that while general attributes of each of the above categories of materials may differ; there may be some common attributes, and any given material may serve multiple purposes within two or more categories of materials.

Dentifrice Composition Comprising Dentifrice Base and Polymer Matrix Films

The film flakes and strips made from the low solubility flavorant-free polymer matrix film are incorporated in the base dentifrice of the present invention, preferably at a concentration of about 0.05 to 1.0% by weight and preferably 0.1 to about 0.5% by weight. The film flakes or strips are generally added to the dentifrice base as a last step, so as to minimize the shear to which the dentifrice ingredients are subjected to during the prior mixing steps.

Initially, the combined compositions comprises low solubility flavorant-free polymer matrix film in the dentifrice base that comprises low solubility flavorant. Over time, the low solubility flavorant transfers from the dentifrice base into the polymer matrix films.

In some embodiments, the film matrix is rupturable during tooth brushing so that one or more additives such as the low solubility flavorant is released when the dentifrice is applied topically to tooth surfaces, the mechanical agitation created during tooth brushing effecting rupture of the film matrix whereby the entrained ingredient is released to the tooth surface. In some embodiments, the complete release is extended such that the flavor experience continues after the oral care procedure is performed.

SPECIFIC EMBODIMENTS

The invention is further described in the following examples. The examples are merely illustrative and do not in any way limit the scope of the invention as described and claimed.

Example 1

A strong cooling signal can be delivered from polymer matrix film which can be manufactured at a much reduced cost by utilizing menthol (or any low solubility flavor ingredient) in the toothpaste base to saturate the polymer matrix film which is manufactured free of the low solubility flavor. The presence of hydrophobic materials in the polymer matrix film facilitated transfer of the flavor from the base to the film.

This approach can be extremely cost effective relative to conventional processes in which about 50% of the flavor in the slurry composition used to make (cast and dry) the films is lost in the drying process. As menthol and other flavor ingredients are expensive, a desirable process is to flavor the film in the toothpaste base through reverse migration of the flavor ingredient(s) of choice.

In-situ mentholation produced by mixing toothpaste base containing menthol with plain or unflavored films provides advantages over manufacturing and adding mentholated films into toothpaste base. The product produced using in situ mentholation provides the same performances as those in which mentholated films are added to the toothpaste base. The technology provides the following advantages:

reduction of formula cost by eliminating menthol loss during the drying process;

reduction of formula cost by elimination of ethanol in the slurry composition;

simplification of the film making process; and improved safety of the film making environment.

The results of several migration studies of menthol from flavored films indicated that menthol in the film can quickly migrate to bulk toothpaste base and eventually reach equilibrium concentrations in the film depending on the composition.

Toothpaste made using flavorant free films can be used to deliver flavored films which provide a cooling sensation or taste benefit because the flavorant will transfer from the toothpaste base to the flavor free film by reverse migration of menthol.

The menthol level in the film can be concentrated at a greater level by the incorporation of hydrophobic materials in the film formula. Using hydrophobic materials in the menthol free film results in a greater transfer of menthol from the base toothpaste migrates to the menthol free film. The resultant dentifrice composition provides a stronger on intense cooling sensation while lowering the cost of materials and manufacturing.

The low solubility flavorant-free polymer matrix film, i.e., polymer matrix film without menthol. The composition of the slurry used to make the menthol free film is listed in Table 1.

TABLE 1

Composition of Plain Film Slurry

| Ingredient | Plain Film Slurry (%) |
|---|---|
| DI Water | 67.91 |
| Methcel E5 | 6.25 |
| Methcel E50 | 5.64 |
| ZnO Powder | 19.89 |
| Tween 80 | 0.31 |

The toothpaste base formulation shown in Table 2, which contains 2000 ppm of menthol.

TABLE 2

| Ingredient | Toothpaste with Plain Film (%) |
|---|---|
| Polyethylene Glycol 600 | 1.00 |
| CMC 500T | 0.55 |
| Sodium Saccharin | 0.35 |
| Sodium Fluoride | 0.32 |
| Sorbitol (70% solution) | 68.00 |
| Purified Water | 9.75 |
| D&C Red No. 30 | 0.01 |
| Silica Zeodent 114 | 8.00 |
| Silica Zeodent 165 | 8.00 |
| Cocaamidopropyl Betaine | 1.25 |
| Sodium Lauryl Sulfate | 1.57 |
| Film | 1.00 |
| Menthol | 0.20 |
| Total | 100.00 |

The toothpaste base which includes menthol was combined with menthol free film strips and aged at room temperature. Films were isolated from base at certain time points. The concentration of menthol in the isolated films was determined by GC-MS. The results are summarized in Table 3.

TABLE 3

| Aged Time | Menthol level in film isolated from toothpaste (ppm) |
|---|---|
| 0 Hour | — |
| 4 Hours | 1194 |
| 8 Hours | 1508 |
| 24 Hours | 1842 |
| 48 Hours | 1967 |
| 72 Hours | 2008 |
| 1 week | 2433 |

The results summarized in Table 3 showed that menthol migrated into the film. If the menthol is evenly distributed in the base and in the film, the concentration of menthol in the film should be the same as in toothpaste, 2000 ppm. At one week, menthol concentration in the film was greater than 2000 ppm.

Slurry composition of menthol free film comprising hydrophobic/lipophilic additives is shown in Table 4.

TABLE 4

| Ingredient | "Menthol concentrating" film slurry (%) |
|---|---|
| DI Water | 67.91 - "c" |
| Methcel E5 | 6.25 |
| Methcel E50 | 5.64 |
| ZnO Powder | 19.89 |
| Hydrophobic/lipophilic additives | "c" |
| Tween 80 | 0.31 |

Illustrative examples of hydrophobic additives suited for inclusion into the composition include, but are not limited to, petrolatum, silicone oil, beeswax, hydrogenated soybean oil, sweet almond oil, peanut oil, avocado oil, borage oil, palmitic acid, cacao butter, carnauba wax, castor oil, coconut oil, evening primrose oil, glycerin, glyceryl stearate, jojoba oil, camphor, Kkaolin, lanolin, cod liver oil, linseed oil, corn oil, olive oil, palm oil, paraffin, squalane, rapeseed oil, rose oil, safflower oil, sesame oil, shea butter, dimethicone silicone oil, tall oil, wheat germ oil, sunflower oil, trimethylsiloxysilicate, alkyldimethylsilyl solypropylsesquioxane, ethyl cellulose polymers, dimethiconol, trimethylsiloxysilicate, polyether-modified silicone, cross-linked polymers, polypropylsilsesquioxane, dimethicone polymers, dimethicone crosspolymer, dimethicone/vinyl dimethicone cross polymers, other fats and oils, and combinations thereof.

Example 2

Five different films were made using different hydrophobic/lipophilic additives.

Formulae of the control film slurry and the additive film slurry were as set forth in Table 5.

TABLE 5

| Ingredient | Control film slurry (%) | Additive film slurry (%) |
|---|---|---|
| DI Water | 73.17 | 73.17 |
| Methcel E5 | 21.00 | 19.00 |
| Saccharin | 1.00 | 1.00 |
| Propylene Glycol | 4.00 | 4.00 |
| Colorant | 0.03 | 0.03 |
| Hydrophobic/Lipophilic Additive | — | 2.00 |
| Tween 80 | 0.80 | 0.80 |
| Total | 100.00 | 100.00 |

The compositions of the film produced were as set forth in Table 6.

TABLE 6

| Ingredient | Control film (%) | Additive film (%) |
| --- | --- | --- |
| DI Water | 2.00 | 2.00 |
| Methcel E5 | 76.71 | 69.40 |
| Saccharin | 3.65 | 3.65 |
| Propylene Glycol | 14.61 | 14.61 |
| Colorant | 0.11 | 0.11 |
| Hydrophobic/Lipophilic Additive | — | 7.31 |
| Tween 80 | 2.92 | 2.92 |
| Total | 100.00 | 100.00 |

The five different films that were made were identified using different colorants associated with the hydrophobic/lipophilic additive used. The colorants, additives and color of the films are set forth in Table 7.

TABLE 7

| Film type | Colorant | Additive | Film color |
| --- | --- | --- | --- |
| Control - White | Titanium Dioxide | None | White |
| Additive film A -Red | Red 30 | Petrolatum | Red |
| Additive film B - Blue | Blue 15 | Silicone Oil | Blue |
| Additive film C - Yellow | Yellow LC128 | Beeswax | Yellow |
| Additive film D - Black | Blue/Red (Ratio --1/2) | Hydrogenated Soybean Oil | Black |

The different discs were combined into tooth paste base shown in Table 8 containing 1.4% Iralia flavorant by weight and 0.5% film weight.

TABLE 8

| Ingredient | Toothpaste with Plain Film (%) |
| --- | --- |
| Polyethylene Glycol 600 | 1.00 |
| CMC 500T | 0.55 |
| Sodium Saccharin | 0.35 |
| Sodium Fluoride | 0.32 |
| Sorbitol (70% solution) | 68.00 |
| Purified Water | 9.05 |
| D&C Red No. 30 | 0.01 |
| Silica Zeodent 114 | 8.00 |
| Silica Zeodent 165 | 8.00 |
| Cocaamidopropyl Betaine | 1.25 |
| Sodium Lauryl Sulfate | 1.57 |
| Film | 0.5 |
| Flavor | 1.4 |
| Total | 100.00 |

Test Procedures:

The transfer of Iralia from the tooth paste base to the low solubility free film was measured.

Preparation of test films: The film was cut into circles with 0.25 inches diameters by using a punch. The circles with the weight of 0.005+/−0.0005 grams/piece were selected for the study. Twenty four pieces of each film were used for the investigation.

Test toothpaste: Iralia was selected as a model flavor ingredient for the study. Base toothpaste and Iralia were mixed at the ratio of 98.1/1.4. The homogeneity of Iralia in the toothpaste was checked by HPLC before adding test film discs. Test toothpaste was made by mixing Iralia toothpaste with film circles at the ratio of 99.5/0.5.

Quantification of Iralia: After two weeks aging at room temperature four circles of each test film were isolated from aged toothpaste. The toothpaste was removed from disc by using a spatula first. Then residue toothpaste on disc surface was rubbed off four times by using a clean tissue. Each piece of cleaned disc was dissolved by adding 10 ml of Acetonitrate/Water (80/20) in a 20 ml vial. The level (c) of Iralia in the solution was determined by HPLC.

Calculation: The level of Iralia in the film was calculated as:

$$C\text{-average \%} = (c_1+c_2+c_3+c_4)/4 \ast 10/W\text{-circle}/10{,}000$$

W-circle is the average weight of the 24 pieces circles of corresponding test film.

Results:

The films were combined with toothpaste base containing the flavorant Iralia and the aged. Levels of Iralia in the film were measured after 2 weeks and 4 weeks. The results are shown in Table 9.

TABLE 9

| Aging @ RT | White film | Red film | Blue film | Yellow film | Black film |
| --- | --- | --- | --- | --- | --- |
| 2 W Iralia level | 1.44% | 3.14% | 2.39% | 2.07% | 3.96% |
| 4 W Iralia level | 2.08% | 4.68% | 3.48% | 3.02% | 5.62% |

What is claimed is:

1. A method of preparing a dentifrice comprising polymer matrix film with low solubility flavorant therein comprising the steps of:
    a) forming a polymer matrix film in the substantial absence of low solubility flavorant, wherein said polymer matrix comprises a water soluble polymer and a hydrophobic/lipophilic additive;
    b) forming a dentifrice base comprising a low solubility flavorant selected from the group consisting of menthol, spearmint oil, cinnamon oil, peppermint oil, clove oil, bay oil, thyme oil, cedar leaf oil, oil of nutmeg, oil of sage, and oil of bitter almonds;
    c) combining the polymer matrix film with the dentifrice base; and
    d) maintaining the combined polymer matrix film and dentifrice base for an amount of time suitable for an amount of low solubility flavorant to transfer from said dentifrice base to said polymer matrix film such that the concentration of the low solubility flavorant in the polymer matrix film is nearly equal to, equal to or greater than the concentration of the low solubility flavorant in the dentifrice base;
    wherein the ratio of water soluble polymer to the hydrophobic/lipophilic additive by weight in the film is from 10.7:1 to 9.3:1; and
    wherein the hydrophobic/lipophilic additive comprises silicone oil, and wherein the amount of hydrophobic/lipophilic additive in the polymer matrix film is about 7% by weight of the film, and wherein the amount of water soluble polymer is 65% to 75% by weight of the film; and
    wherein the dentifrice comprises the film in an amount of 1% by weight of the dentifrice.

2. The method of claim 1 wherein the low solubility flavorant is menthol.

3. The method of claim 1 wherein the polymer matrix film further comprises one or more additional hydrophobic/lipophilic additives selected from the group consisting of: petrolatum, beeswax, hydrogenated soybean oil, sweet almond oil, peanut oil, avocado oil, borage oil, palmitic acid, cacao butter, carnauba wax, castor oil, coconut oil, evening primrose oil, glycerin, glyceryl stearate, jojoba oil, camphor, kaolin, lanolin, cod liver oil, linseed oil, corn oil, olive oil, palm oil, paraffin, squalane, rapeseed oil, rose oil, safflower oil, sesame oil, shea butter, dimethicone silicone oil, tall oil, wheat germ oil, sunflower oil, and combinations thereof.

4. The method of claim 1 wherein the polymer matrix film comprise a cellulose polymer.

5. The method of claim 4 wherein said cellulose polymer comprises hydroxypropyl methyl cellulose.

6. The method of claim 1 wherein the polymer matrix film further comprises one or more additional components selected from the group consisting of: diols, surfactants, starches, colorants, dyes, sweeteners, whitening agents, breath freshening agents, abrasives, cationic prophylactic and therapeutic agents, fluoride ion sources, stannous ion sources, tartar control agents, antimicrobial agents, antioxidants, saliva stimulating agents, antiplaque agents, anti-inflammatory agents, H2 antagonists, desensitizing agents, nutrients, and proteins.

7. The method of claim 1 wherein the dentifrice base further comprises one or more additional components selected from the group consisting of: diols, surfactants, starches, colorants, dyes, sweeteners, whitening agents, breath freshening agents, abrasives, cationic prophylactic and therapeutic agents, fluoride ion sources, stannous ion sources, tartar control agents, antimicrobial agents, antioxidants, saliva stimulating agents, antiplaque agents, anti-inflammatory agents, H2 antagonists, desensitizing agents, nutrients, and proteins.

8. The method of claim 1 wherein step a) comprises the steps of:

forming a low solubility flavorant free polymer matrix film by forming a slurry comprising a water soluble polymer and no low solubility flavorant, dispensing the slurry on a surface wherein the slurry forms a layer of slurry on the surface, and drying the layer of slurry to produce the low solubility flavorant free polymer matrix film.

9. The method of claim 8 further comprising the step of after drying the slurry layer to form the low solubility flavorant free polymer matrix film, cutting or punching the low solubility flavorant free polymer matrix film to form film flakes or strips of low solubility flavorant free polymer matrix film prior to combining the film with the dentifrice base.

10. The method of claim 1 wherein the polymer matrix film that is formed comprises Hydroxypropylmethyl Cellulose, ZnO Powder and Polysorbate.

11. The method of claim 1 wherein the polymer matrix film is formed in the substantial absence of alcohol.

12. The method of claim 1 wherein the dentifrice base that is formed comprises: Polyethylene Glycol 600, Carboxymethyl Cellulose, Sodium Saccharin, Sodium Fluoride, Sorbitol, Purified Water, D&C Red No. 30, Silica Zeodent, Cocaamidopropyl Betaine, Sodium Lauryl Sulfate and Menthol.

13. The method of claim 1 wherein the combined polymer matrix film and dentifrice base comprises about 0.2% menthol.

* * * * *